United States Patent [19]

Kawagishi et al.

[11] Patent Number: 4,774,172
[45] Date of Patent: Sep. 27, 1988

[54] SILVER HALIDE COLOR PHOTOGRAPHIC MATERIALS

[75] Inventors: Toshio Kawagishi; Takayoshi Kamio; Keizo Kimura; Tadahisa Sato; Nobuo Furutachi, all of Kanagawa, Japan

[73] Assignee: Fuji Photo Film Co., Ltd., Kanagawa, Japan

[21] Appl. No.: 935,987

[22] Filed: Nov. 28, 1986

[30] Foreign Application Priority Data

Nov. 27, 1985 [JP] Japan .................... 60-266796

[51] Int. Cl.$^4$ ............................................. G03C 7/38
[52] U.S. Cl. .................................. 430/558; 430/386; 430/387
[58] Field of Search ................ 430/558, 386, 387, 551

[56] References Cited

U.S. PATENT DOCUMENTS 4,548,899 10/1985 Nakayama et al. ............ 430/387
4,639,415 1/1987 Kaneko et al. ................ 430/558
4,659,652 4/1987 Kawagishi et al. ............ 430/558

Primary Examiner—Richard L. Schilling
Attorney, Agent, or Firm—Sughrue, Mion, Zinn, Macpeak & Seas

[57] ABSTRACT

Silver halide color photographic materials are described, which comprise at least one silver halide emulsion layer coated on a support and which are characterized by the incorporation of a pyrazoloazole type coupler of the following general formula (I) into the silver halide emulsion layer(s) or the adjacent layer(s) thereto:

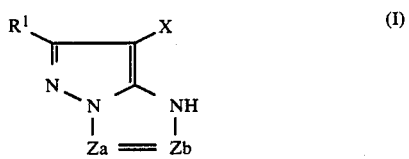

(I)

wherein Za and Zb each may represent

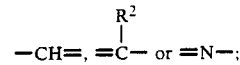

$R^1$ and $R^2$ each may represent a hydrogen atom or a substituent; X represents a hydrogen atom or a group capable of being removed upon a coupling reaction with an oxidized form of an aromatic primary amine type developing agent; when Za=Zb is a carbon-carbon double bond, this may be a part of the aromatic ring in the formula: with the proviso that at least one of $R^1$ and $R^2$ is a group represented by general formulae (II) or (III):

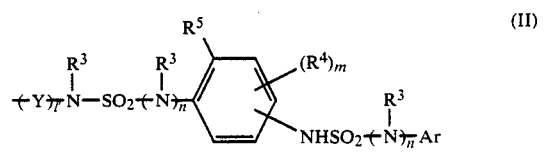

(II)

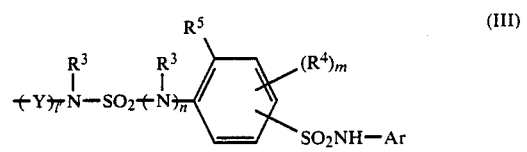

(III)

wherein $R^3$ represents a hydrogen atom or a substituted or unsubstituted alkyl group; $R^4$ represents a hydrogen atom or a substituent; $R^5$ represents a halogen atom, a substituted or unsubstituted alkoxy, aryloxy, amino, alkylthio or arylthio group; Ar represents an aryl group; Y represents an alkylene group or an arylene group; l' is an integer of 0 or 1; n is an integer of 0 or 1; and m is an integer of 1 to 3; and that when $R^1$ represents an alkyl group or Y represents an alkylene group, the alkyl or alkylene group is a group of which the carbon atom directly bonded to the pyrazoloazole nucleus is a primary carbon.

The pyrazoloazole type magenta couplers of general formula (I) may form azomethine dyes with improved color reproducibility and high light fastness. The present silver halide color photographic materials containing the coupler of general formula (I) have excellent colorability and excellent light fastness.

9 Claims, No Drawings

SILVER HALIDE COLOR PHOTOGRAPHIC MATERIALS

FIELD OF THE INVENTION

The present invention relates to silver halide color photographic materials and, more precisely, to those with an improved colorability and an improved color image fastness to light.

BACKGROUND OF THE INVENTION

It is well known that the color development of silver halide color photographic materials is followed by a coupling reaction between an oxidized aromatic primary amine type color developing agent and a coupler contained in the material to form an indophenol, indaniline, indamine, azomethine, phenoxazine, phenazine or the like dye to thereby form a color image in the material. 5-Pyrazolone, cyanoacetophenone, indazolone, pyrazolobenzimidazole or pyrazolotriazole type couplers may be used for the formation of magenta color images.

Almost all the magenta color image forming couplers which have heretofore been studied and have been widely practically used are 5-pyrazolone type couplers. Although the dyes formed from the 5-pyrazolone type couplers have high fastness to heat and light, it is also known that these have an undesirable yellow component due to side-absorption of light at a wavelength of 430 nm or so, which causes color staining in the formed dyes.

Some magenta color image forming coupler skeletons with a reduced yellow component have heretofore been proposed, including, for example, pyrazolobenzimidazole skeletons as described in British Pat. No. 1,047,612; indazolone skeletons as described in U.S. Pat. No. 3,770,447; or 1H-pyrazolo[5,1-c][1,2,4]triazole skeletons as described in U.S. Pat. No. 3,725,067. Further, some other skeletons have recently been proposed, including, for example, 1H-imidazo[1,2-b]pyrazole skeletons as described in European Pat. No. 119,741; 1H-pyrazolo[1,5-b][1,2,4]triazole skeletons as described in European Pat. No. 119,960; 1H-pyrazolo[1,5-d]tetrazole skeletons as described in *Research Disclosure*, No. 24220 (June, 1984); and 1H-pyrazolo[1,5-b]pyrazole skeletons as described in *Research Disclosure*, No. 24230 (June, 1984).

In particular, the magenta dyes formed from 1H-pyrazolo[5,1-c][1,2,4]triazole type couplers as described in U.S. Pat. No. 3,725,067, British Pat. Nos. 1,252,418 and 1,334,515; 1H-imdazo[1,2-b]pyrazole type couplers as described in European Pat. No. 119,741; 1H-pyrazolo[1,5-b][1,2,4]triazole type couplers as described in European Pat. No. 119,860; 1H-pyrazolo[1,5-d]tetrazole type couplers as described in *Research Disclosure*, No. 24220 (June, 1984); and 1H-pyrazolo[1,5-b]pyrazole type couplers as described in *Research Disclosure*, No. 24230 (June, 1984), among the above-mentioned dyes, have excellent absorption characteristics with no side-absorption in the visible range, in a solvent such as ethyl acetate or dibutyl phthalate.

However, these couplers are still disadvantageous in that the colorability is low and the color images formed therefrom have an insufficient light fastness. In order to improve the colorability, the introduction of a sulfonamidophenylenesulfonyl group into the pyrazoloazole ring-containing molecules, such as described in Japanese Patent Application (OPI) No. 177557/84 (the term "OPI" as used herein refers to a "published unexamined Japanese patent application"), is somewhat effective, but this is still insufficient for use in color photographic materials, especially in those for prints.

Pyrazoloazole couplers whose pyrazoloazole nucleus contains a branched alkyl group at the 2-, 3- or 6-position thereof and a sulfonamidophenylenesulfonyl group at the 2-, 3- or 6-position thereof show improved fastness of color images to light but have problems that fog during development processing increases to some extent and yield of ring formation is low.

SUMMARY OF THE INVENTION

Accordingly, a first object of the present invention is to provide silver halide color photographic materials with improved color image fastness to light by the incorporation therein of a pyrazoloazole type magenta coupler which may form an azomethine dye with improved color reproducibility and a high light fastness.

A second object of the present invention is to provide silver halide color photographic materials with excellent colorability with less fog formation during development processing.

In order to attain the above-mentioned objects, the present invention provides a silver halide color photographic material which comprises at least one silver halide emulsion layer provided on a support and which is characterized by the incorporation of a pyrazoloazole type coupler of the following general formula (I) into at least one of the silver halide emulsion layer(s) or the adjacent layer(s) thereto:

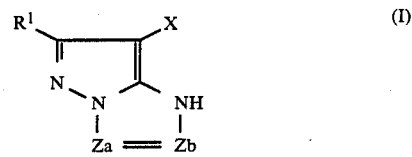

wherein Za and Zb each may represent

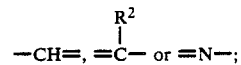

$R^1$ and $R^2$ each may represent a hydrogen atom or a substituent; X represents a hydrogen atom or a group capable of being removed upon a coupling reaction with an oxidized form of an aromatic primary amine type developing agent; when Za=Zb is a carbon-carbon double bond, this may be a part of the aromatic ring in the formula; with the proviso that at least one of $R^1$ an $R^2$ is a group represented by general formulae (II) or (III):

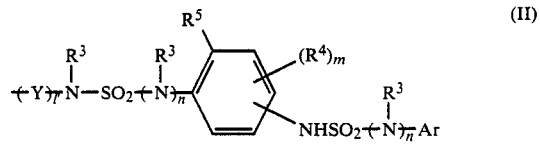

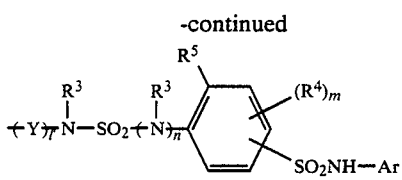

(III)

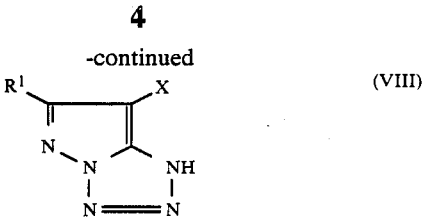

(VIII)

wherein $R^3$ represents a hydrogen atom or a substituted or unsubstituted alkyl group; $R^4$ represents a hydrogen atom or a substituent; $R^5$ represents a halogen atom, a substituted or unsubstituted alkoxy, aryloxy, amino, alkylthio or arylthio group; Ar represents an aryl group; Y represents an alkylene group or an arylene group; $l'$ is an integer of 0 or 1; n is an integer of 0 or 1; and m is an integer of 1 to 3; and that when $R^1$ represents an alkyl group or Y represents an alkylene group, the alkyl or alkylene group is a group of which the carbon atom directly bonded to the pyrazoloazole nucleus is a primary carbon.

DETAILED DESCRIPTION OF THE INVENTION

The term "primary carbon" as used herein means that the carbon atom has two or three hydrogen atoms bonded thereto.

Preferred compounds among the pyrazoloazole type magenta couplers of general formula (I) are those represented by the following general formulae (IV), (V), (VI), (VII) or (VIII):

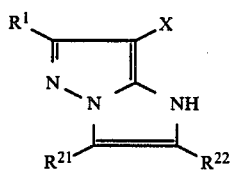

(IV)

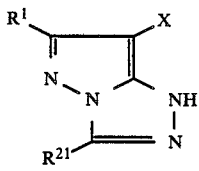

(V)

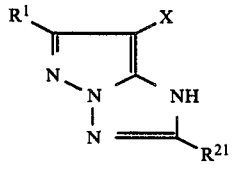

(VI)

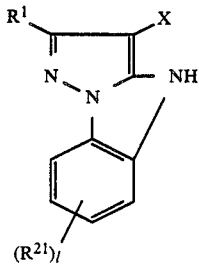

(VII)

In the above general formulae (IV) through (VIII), $R^1$ and X have the same meanings as those with respect to general formula (I); $R^{21}$ and $R^{22}$ have the same meanings as $R^2$ in general formula (I); and l is an integer of 1 to 4.

The substituents in the pyrazoloazole type couplers of general formulae (IV) through (VIII) are explained in detail hereinafter.

More specifically, $R^1$, $R^{21}$ and $R^{22}$ each represents a hydrogen atom, a halogen atom (such as a chlorine atom, a bromine atom or a fluorine atom), a substituted or unsubstituted alkyl group (such as a methyl group, an ethyl group, a trifluoromethyl group, a dodecyl group, a 3-(2,4-di-tert-amylphenoxy)propyl group, an allyl group, a 2-dodecyloxyethyl group, a cyclopentyl group or a benzyl group), an aryl group (such as a phenyl group, a 4-t-butylphenyl group, a 2,4-di-t-amylphenyl group or a 4-tetradecanamidophenyl group), a heterocyclic group, preferably 5- to 7-membered and containing N, O or S as hetero atom(s) (such as a 2-furyl group, a 2-thienyl group, a 2-pyrimidinyl group or a 2-benzothiazolyl group), a cyano group, a hydroxyl group, a substituted or unsubstituted alkoxy group (such as a methoxy group, an ethoxy group, an i-propoxy group, a 2-methoxyethoxy group, a 2-dodecyloxyethoxy group or a 2-methanesulfonylethoxy group), an aryloxy group (such as a phenoxy group, a 2-methylphenoxy group or a 4-t-butylphenoxy group), a heterocyclic oxy group, preferably having a 5- to 7-membered heterocyclic ring containing N, O or S as hetero atom(s) (such as a 2-benzimidazolyloxy group), an acyloxy group (such as an acetoxy group or a hexadecanoyloxy group), a carbamoyloxy group (such as an N-phenylcarbamoyloxy group or an N-ethylcarbamoyloxy group), a silyloxy group (such as a trimethylsilyloxy group), a sulfonyloxy group (such as a dodecylsulfonyloxy group), an acylamino group (such as an acetamido group, a benzamido group, a tetradecanamido group, an α-(2,4-di-t-amylphenoxy)butyramido group, a γ-(3-t-butyl-4-hydroxyphenoxy)butyramido group or an α-[4-(4-hydroxyphenylsulfonyl)phenoxy]decanamido group), an anilino group (such as a phenylamino group, a 2-chloroanilino group, a 2-chloro-5-tetradecanamidoanilino group, a 2-chloro-5-dodecyloxycarbonylanilino group, an N-acetylanilino group or a 2-chloro-5-[α-(3-t-butyl-4-hydroxyphenoxy)dodecanamido]anilino group), an amino group (such as an ethylamino group, a dimethylamino group or a methyloctylamino group), a ureido group (such as a phenylureido group, a methylureido group, an N,N-dimethylureido group or an N,N-dibutylureido group), an imido group (such as an N-succinimido group, a 3-benzylhydantoinyl group or a 4-(2-ethylhexanoylamino)phthalimido group), a sulfamoylamino group (such as an N,N-dipropylsulfamoylamino group or an N-methyl-N-decylsulfamoylamino group), a substituted or unsubstituted alkylthio group (such as a methylthio group, an octylthio group, a tetradecylthio group, a 2-phenoxyethylthio group, a 3-phenoxypropylthio group or a 3-(4-t-butylphenoxy)propylthio group), an arylthio group (such as a phenylthio group, a 2-butoxy-5-t-octylphenylthio group, a 3-pentadecylphenylthio group, a 2-carboxyphenylthio group or a 4-tetradecanamidophenylthio group), a heterocyclic thio group, preferably having a 5- to 7-membered heterocyclic ring containing N, O or S as hetero atom(s) (such as a 2-benzothiazolylthio group), a substituted or unsubstituted alkoxycarbonylamino group (such as a methoxycarbonylamino group or a tetradecyloxycarbonylamino group), a aryloxycarbonylamino group (such as a phenoxycarbonylamino group or a 2,4-di-tert-butylphenoxycarbonylamino group), a sulfonamido group (such as a methanesulfonamido group, a hexadecanesulfonamido group, a benzenesulfonamido group, a p-toluenesulfonamido group, an octadecanesulfonamido group or a 2-methoxy-5-t-butylbenzenesulfonamido group), a carboxyl group, a carbamoyl group (such as an N-ethylcarbamoyl group, an N,N-dibutylcarbamoyl group, an N-(2-dodecyloxyethyl)carbamoyl group, an N-methyl-N-dodecylcarbamoyl group or an N-[3-(2,4-di-tert-amylphenoxy)propyl]carbamoyl group), an acyl group (such as an acetyl group, a (2,4-di-tert-amylphenoxy)acetyl group or a benzoyl group), a sulfamoyl group (such as an N-ethylsulfamoyl group, an N,N-dipropylsulfamoyl group, an N-(2-dodecyloxyethyl)sulfamoyl group, an N-ethyl-N-dodecylsulfamoyl group or an N,N-diethylsulfamoyl group), a sulfonyl group (such as a methanesulfonyl group, an octanesulfonyl group, a benzenesulfonyl group or a toluenesulfonyl group), a sulfinyl group (such as an octanesulfinyl group, a dodecylsulfinyl group or a phenylsulfinyl group), a substituted or unsubstituted alkoxycarbonyl group (such as a methoxycarbonyl group, a butyloxycarbonyl group, a dodecyloxycarbonyl group or an octadecyloxycarbonyl group) or an aryloxycarbonyl group (such as a phenyloxycarbonyl group or a 3-pentadecylphenyloxycarbonyl group).

In general formulae (IV), (V), (VI), (VII) and (VIII), X represents a hydrogen atom, a halogen atom (such as a chlorine atom, a bromine atom or an iodine atom), a carboxyl group, a group bonded via an oxygen atom (such as an acetoxy group, a propanoyloxy group, a benzoyloxy group, a 2,4-dichlorobenzoyloxy group, an ethoxyoxaloyloxy group, a pyruvinyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group or a 2-benzothiazolyloxy group), a group bonded via a nitrogen atom (such as a benzenesulfonamido group, an N-ethyltoluenesulfonamido group, a heptafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-3-oxazolidinyl group, a 1-benzylethoxy-3-hydantoinyl group, a 2N-1,1-dioxo-3(2H)-oxo-1,2-benzisothiazolyl group, a 2-oxo-1,2-dihydro-1-pyridinyl group, an imidazolyl group, a pyrazolyl group, a 4-chloro-1-pyrazolyl group, a 3,5-diethyl-1,2,4-triazol-1-yl group, a 3-chloro-1,2,4-triazol-1-yl group, a 5- or 6-bromobenzotriazol-1-yl group, a 5-methyl-1,2,3,4-triazol-1-yl group, a benzimidazolyl group, a 3-benzyl-1-hydantoinyl group, a 1-benzyl-5-hexadecyloxy-3-hydantoinyl group or a 5-methyl-1-tetrazolyl group), an arylazo group (such as a 4-methoxyphenylazo group, a 4-pivaloylaminophenylazo group, a 2-naphthylazo group or a 3-methyl-4-hydroxyphenylazo group), a group bonded via a sulfur atom (such as a phenylthio group, a 2-carboxyphenylthio group, a 2-butoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-tert-octylphenylthio group, a benzylthio group, a 2-cyanoethylthio group, a 1-ethoxycarbonyltridecylthio group, a 5-phenyl-2,3,4,5-tetrazolylthio group, a 2-benzothiazolylthio group, a 2-dodecylthio-5-thiophenylthio group or a 2-phenyl-3-dodecyl-1,2,4-triazolyl-5-thio group).

Compounds represented by general formulae (IV), (V) and (VI) are especially preferred among the compounds of general formulae (IV) through (VIII). The compounds represented by general formula (VI) are most preferred.

The substituents as represented by general formulae (II) and (III) are explained in detail hereafter. The substituents of general formulae (II) or (III) may be the same as $R^1$, $R^{21}$ or $R^{22}$ in the aforesaid general formulae (IV) through (VIII), or otherwise, may be a group bonded to the appropriate atom of $R^1$, $R^{21}$ and $R^{22}$.

In general formulae (II) and (III), $R^3$ represents a hydrogen atom or a substituted or unsubstituted alkyl group (such as a methyl group, an ethyl group, an n-hexyl group, a 2-ethylhexyl group, a 2-dodecyloxyethyl group, a benzyl group or a 2-methanesulfonylethyl group); $R^4$ represents a hydrogen atom or the same substituents as $R^1$, $R^{21}$ or $R^{22}$, defined above; Ar represents, for example, a substituted or unsubstituted phenyl group or naphthyl group, and more precisely, a phenyl group, an α- or β-naphthyl group, a 2-chlorophenyl group, a 4-tert-octylphenyl group, a 4-dodecyloxyphenyl group, a 2,4-didodecyloxyphenyl group, a 2-chloro-5-tetradecanamidophenyl group, a 2-octyloxy-5-tert-octylphenyl group, a 3,5-didodecylsulfamoylphenyl group, a 3,5-bis(2-ethylhexyloxycarbonyl)phenyl group, a 2,5-dioctyloxyphenyl group or a 4-dodecylphenyl group; $R^5$ represents a halogen atom (such as a fluorine atom, a chlorine atom or a bromine atom), a substituted or unsubstituted alkoxy group (in which the alkyl residue may be linear, branched or cyclic, or may be a saturated alkyl residue or an unsaturated alkyl residue) (such as a methoxy group, a butoxy group, a hexyloxy group, an octyloxy group, an allyloxy group, a 2-dodecylthioethoxy group, a 2-propionoxy group, a 2-methoxyethoxy group or a 2-(N,N-diethylamino)ethoxy group), an aryloxy group (such as a phenoxy group, a 2-methoxyphenoxy group, a 4-tert-butylphenoxy group or a 2-phenylphenoxy group), an amino group (such as an unsubstituted amino group, an N,N-dimethylamino group, an N-methyl-N-butylamino group, a pyrrolidinyl group, a morpholino group, an N-methylanilino group, a 2-chloroanilino group, a 2-methoxy-5-methylanilino group, an N,N-dibutylamino group or an N,N-bis(2-propyloxyethyl)amino group), a substituted or unsubstituted alkylthio group (in which the alkyl residue may be linear, branched or cyclic) (such as a dodecyl group, a 2-butoxyethylthio group, a 2-(N,N-diethyl)aminoethylthio group or a 2-[2-(2-ethoxy)ethoxy]ethylthio group) or an arylthio group (such as a phenylthio group, a 2-butoxyphenylthio group, a 4-tert-octylphenylthio group or a 2-butoxy-5-tert-octylphenylthio group).

Among the substituents represented by general formulae (II) and (III), those where $R^3$ is hydrogen are most preferred.

Among the compounds represented by general formulae (I), (II) and (III), those where at least one of $R^1$ and Y represents an alkyl group or an alkylene group are particularly preferred.

Examples of the couplers of the present invention are shown hereafter; however, the couplers of the present invention are not limited in scope by the following specific examples thereof:

(1)

(2)

(3)

(4)

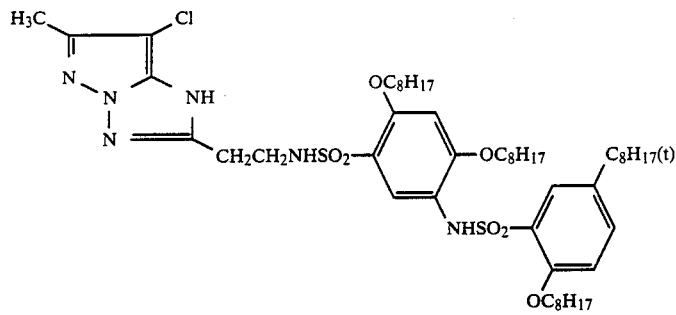
(5)
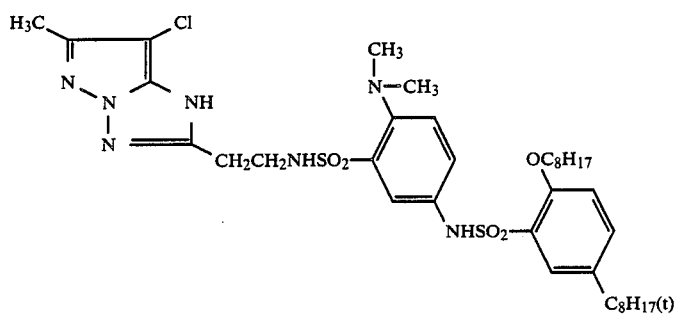
(6)
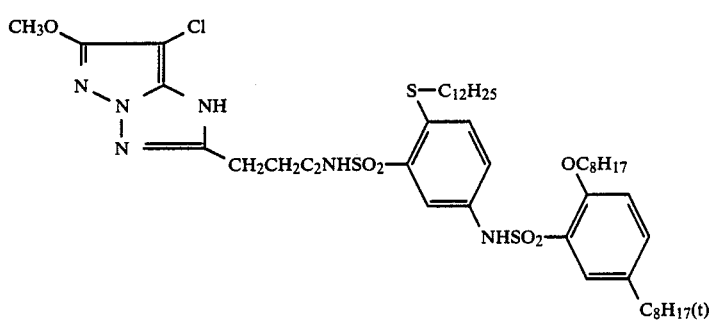
(7)
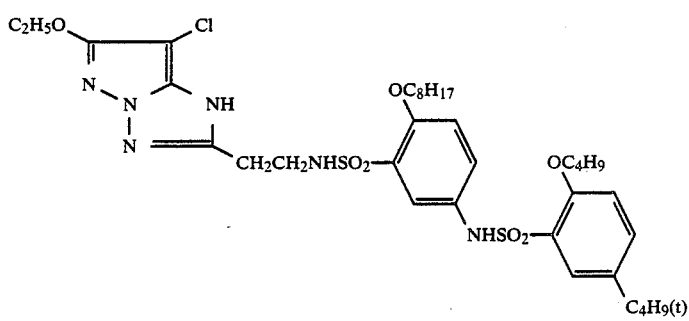
(8)
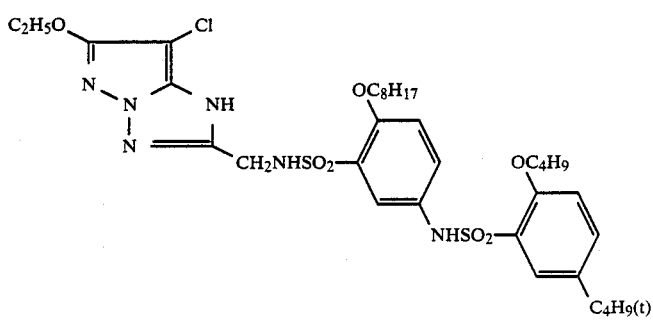
(9)

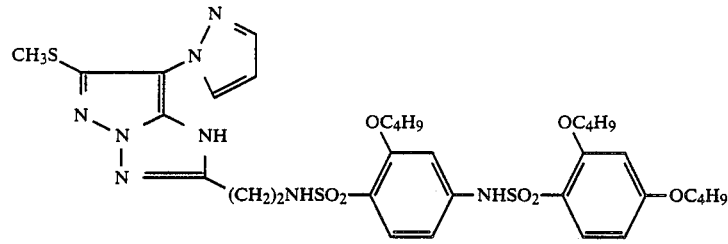
(10)
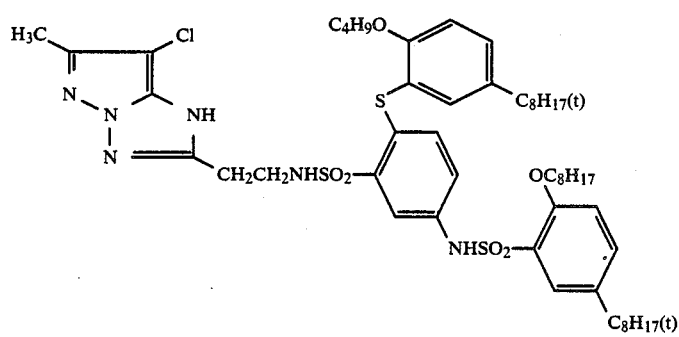
(11)
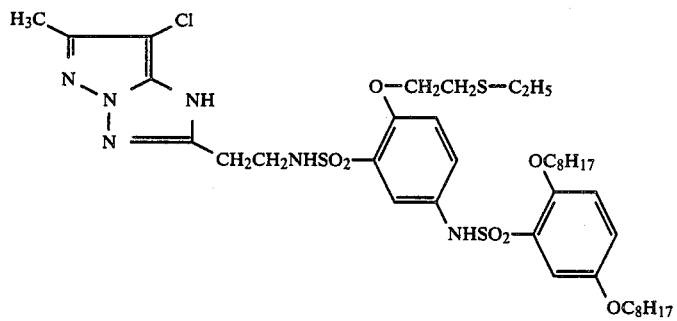
(12)
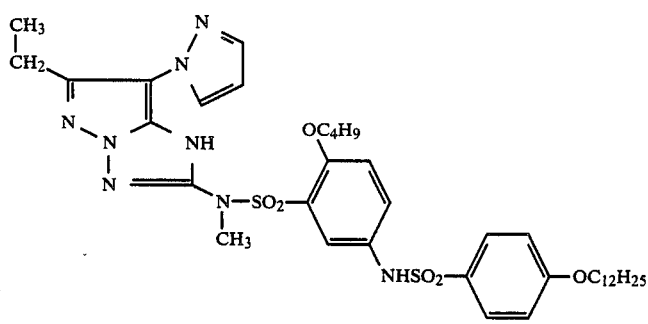
(13)
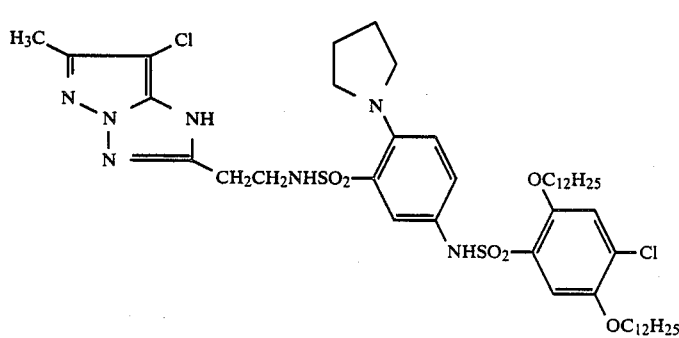
(14)

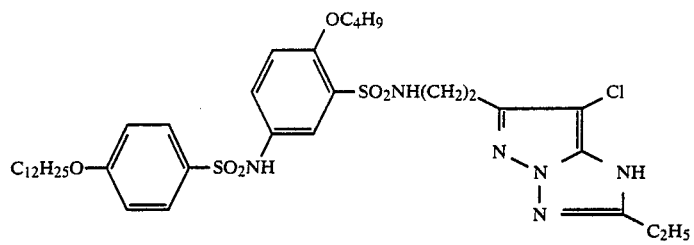
(15)
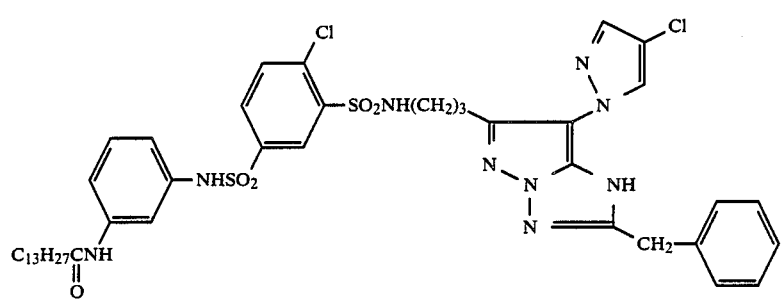
(16)
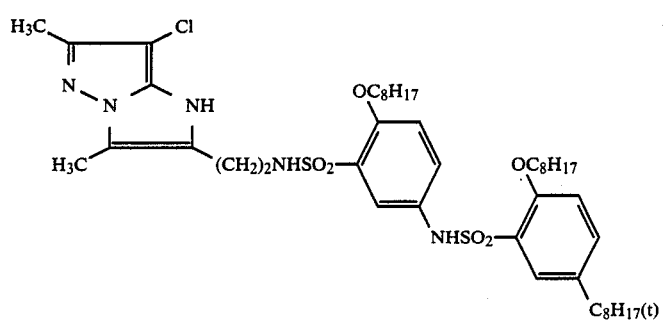
(17)
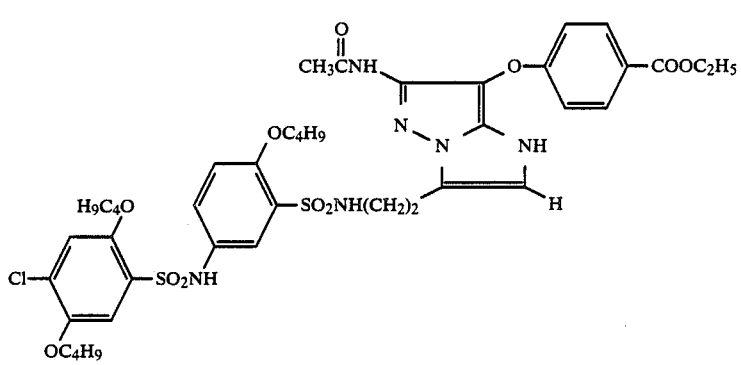
(18)
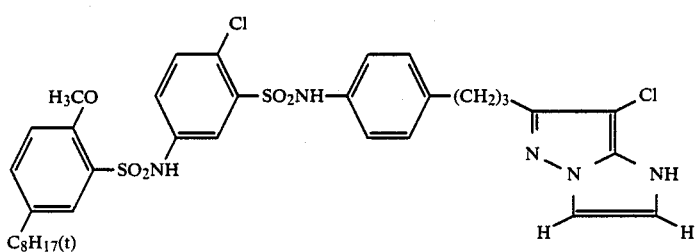
(19)

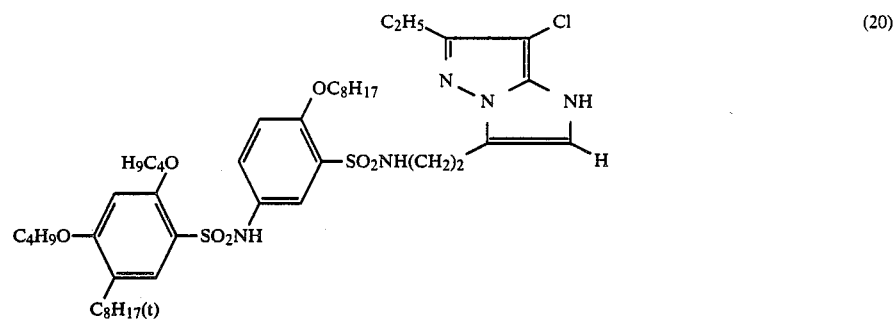
(20)
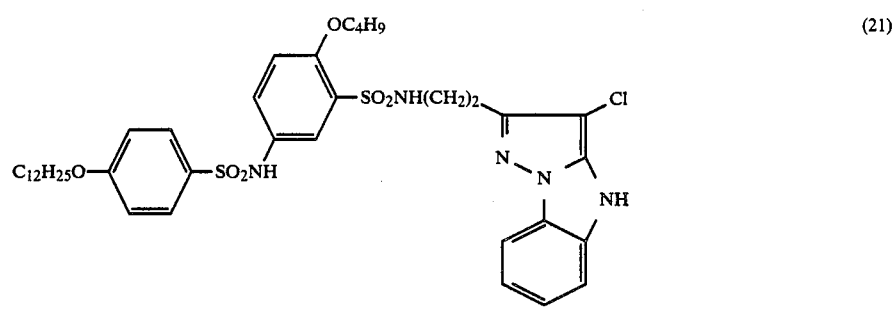
(21)
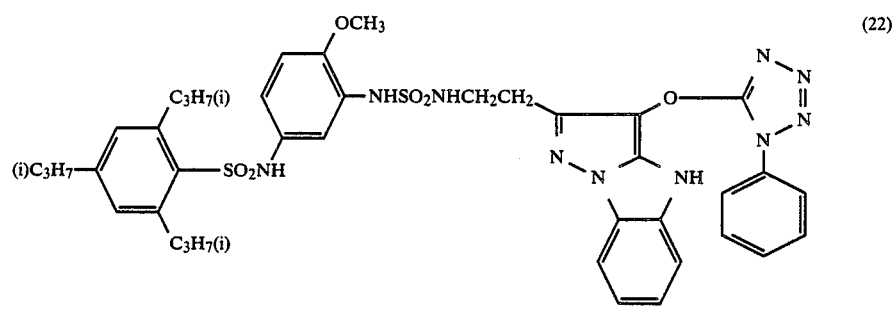
(22)
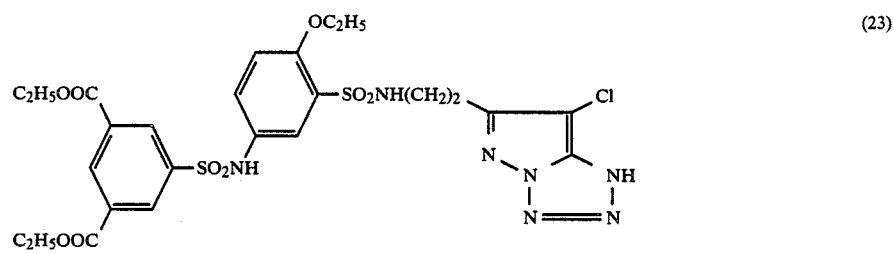
(23)
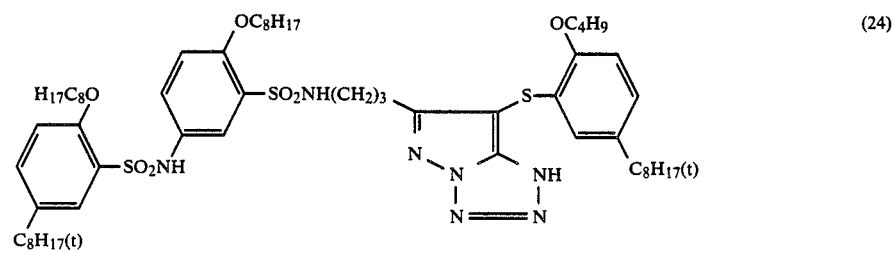
(24)

-continued
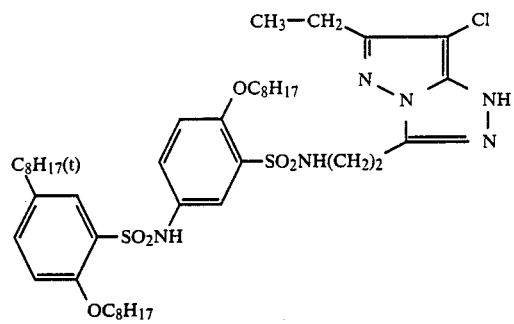
(25)
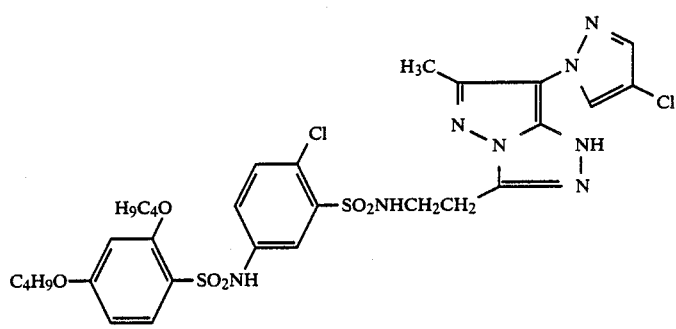
(26)
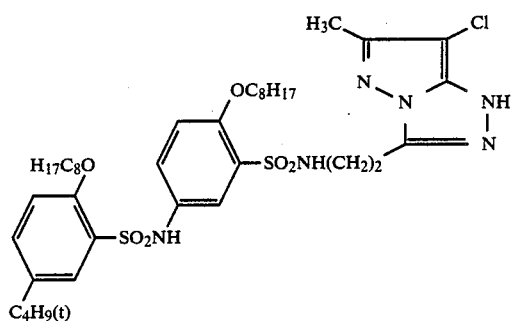
(27)
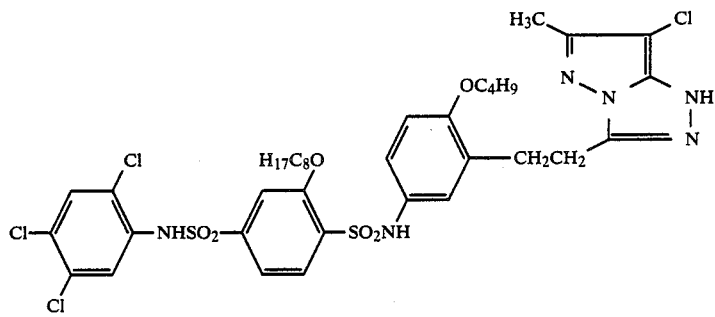
(28)
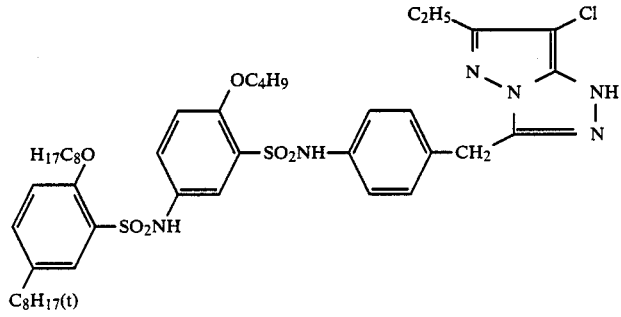
(29)

-continued

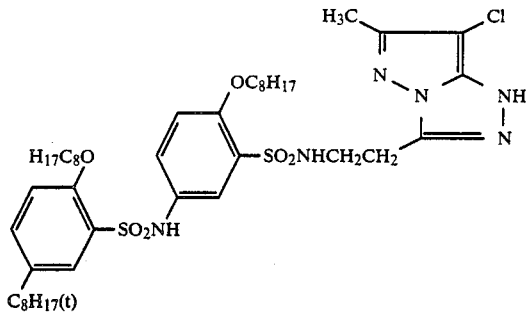
(30)

Some examples are described herein to illustrate the synthesis of the couplers of the present invention. Couplers in accordance with the present invention, other than the ones illustrated below, may also be synthesized in an analogous manner.

SYNTHESIS EXAMPLE
Synthesis of Coupler No. (1) Shown Above to the resulting solution for crystallization to obtain 45.6 g of Coupler No. (1). Yield: 72%. m.p.: 106°–107° C.

The silver halide color photographic materials of the present invention can be prepared in a conventional manner using in addition to the pyrazoloazole coupler represented by general formula (I) various conventional additives and elements as described below.

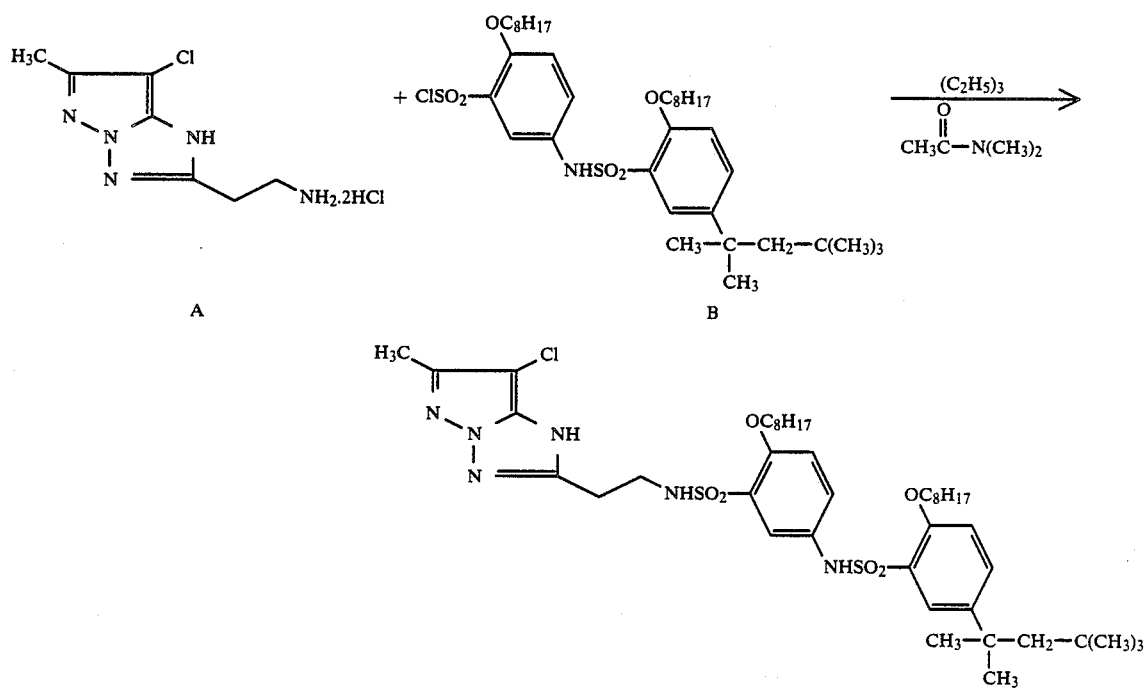

Coupler No. (1)

2-(2-Aminoethyl)-7-chloro-6-methylpyrazolo[1,5-b][1,2,4]triazole dihydrochloride (A) (20 g) was dissolved in 100 ml of dimethylacetamide. The resulting solution was cooled with an ice water bath, and then 34 ml of triethylamine was added thereto and stirred for 10 minutes. To this solution was dropwise added a solution of 51.4 of 5-(5-t-octyl-2-octyloxybenzenesulfonamido)-2-octyloxybenzenesulfonyl chloride (B) as dissolved in acetonitrile (100 ml) in the course of 30 minutes. This resulting solution was stirred for 30 minutes and then the reaction mixture was poured into 400 ml of water and thereafter extracted with 200 ml of ethyl acetate. The organic layer was washed twice with 150 ml of salt solution and then dried with anhydrous magnesium sulfate. The ethyl acetate solution was concentrated to dryness and the residue was then dissolved in 50 ml of ethyl acetate under heat. 300 ml of n-hexane was added

| Additive/Element/Method | Reference |
|---|---|
| (1) Color image stabilizing agent | U.S. Pat. No. 4,540,654, col. 41, lines 6–47 |
| (2) Method of adding couplers | Ibid., col. 42, lines 41 to col. 43, line 28 |
| (3) Color fog preventing agent | Ibid., col. 43, lines 40–51 |
| (4) Ultraviolet ray absorbing agent | Ibid., col. 43, lines 52 to col. 44, line 6 |
| (5) A water-soluble dye as a filter dye or for the purpose of preventing irradiation or other various purposes | Ibid., col. 44, lines 7–21 |
| (6) A spectral sensitizing dye | Ibid., col. 44, line 22 to col. 45, line 16 |
| (7) A color developing solution and a color | Ibid., col. 45, lines 17–42 |

| Additive/Element/Method | Reference |
|---|---|
| developing agent | |
| (8) Other additives to color developer | Ibid., col. 45, lines 43–59 |
| (9) Bleach (blix) process and a bleaching agent | Ibid., col. 45, line 60 to col. 46, line 11 |
| (10) A bleaching accelerator | Ibid., col. 46, lines 12–17 |
| (11) Halogen composition of silver halide emulsion | Ibid., col. 46, lines 23–26 |
| (12) Grain size distribution and crystal form of silver halide | Ibid., col. 46, lines 32–36 (Grain size distribution is preferably 0.15 or less in terms of a variation coefficient.) |
| (13) Method for producing silver halide emulsion | Ibid., col. 46, line 37 to col. 47, line 6 |
| (14) Additives for grain formation and/or physical ripening of silver halide emulsion | Ibid., col. 47, lines 7–11 |
| (15) Chemical sensitization | Ibid., col. 47, lines 26–34 |
| (16) A surface active agent | Ibid., col. 47, line 35 to col. 48, line 3 |
| (17) A yellow coupler | U.S. Pat. No. 4,607,002 2-Equivalent couplers represented by general formula (II) as described in col. 9, line 25 to col. 10, line 64, corresponding 4-equivalent couplers and polymer couplers derived therefrom. Specific examples of the couplers represented by general formula (II), Y-1 to Y-25 are described in col. 11 to col. 15, line 12. |
| (18) A cyan coupler | U.S. Pat. No. 4,607,002 2-Equivalent couplers represented by general formulae (III) and/or (IV) as described in col. 15, line 15 to col. 16, line 40, corresponding 4-equivalent couplers and polymer couplers derived therefrom. Specific examples of the couplers represented by general formula (III), C-(I)-1 to -12, are described in col. 16, line 41 to col. 18, line 35, and those of the couplers represented by general formula (IV), C-(II)-1 to -10, are described in cols. 17–20. Other useful cyan couplers include those represented by general formula (I) described in col. 1, line 55 to col. 3, line 43 of U.S. Pat. No. 4,327,173. Specific examples thereof, Couplers (1) to (28) are described in col. 3, line 50 to col. 6, line 34. Further, useful cyan couplers include those represented by general formulae [I], [II], [III] or [IV] as described in col. 2, line 1 to col. 4, line 52 of U.S. Pat. No. 4,430,423. Specific examples thereof, Compounds (1) to (17), are described in col. 5, line 10 to col. 7, line 10. |

U.S. Pat. Nos. 4,540,654, 4,607,002, 4,327,173 and 4,430,423 are incorporated herein by reference.

As for the support constituting the light-sensitive material of the present invention, there can be used plastic film, plastic laminated paper, baryta paper, synthetic paper, etc. Also, reflective supports can be used which comprise a substrate provided with, for example, a thin metal film or a layer filled with metal powders so that the surface thereof can have a mirror-surface reflectivity or second degree reflectivity.

The silver halide color photographic material of the present invention contains the pyrazoloazole coupler represented by general formula (I) preferably in an amount of from about 0.003 to about 0.3 mol per mol of silver halide in the green-sensitive emulsion layer.

The pyrazoloazole coupler represented by general formula (I) can be added to one or more silver halide emulsion layers or light-insensitive hydrophilic colloid layer(s) adjacent thereto containing gelatin as a major binder component.

The present invention will be explained in greater detail by reference to the following examples, which, however, are not intended to be interpreted as limiting the scope of the present invention in any manner. Unless otherwise indicated, all parts, percents, ratios and the like are by weight.

EXAMPLE 1

Tricresyl phosphate (8.8 mg), 8.6 ml of tris(2-ethylhexyl)phosphate and 25 ml of ethyl acetate were added to 8.8 g of Coupler No. (4) and dissolved under heat, and the resulting solution was added to 100 ml of an aqueous solution containing 10 g of gelatin and 1.0 g of sodium dodecylbenzenesulfonate and rapidly stirred to obtain a finely emulsified dispersion of Coupler No. (4). All of this emulsified dispersion was added to 100 g of a silver chlorobromide emulsion (Br content: 50 mol%, Ag content: 6.5 g), and 10 ml of 2% sodium 2,4-dihydroxy-6-chloro-s-triazine, as a hardener, as added thereto. The resulting solution was coated on a paper support, which had been laminated with polyethylene on both surfaces, the coated silver amount being 200 mg/m². A gelatin layer was superposed on the thus coated emulsion layer to obtain Sample (A).

In the same manner as Sample (A) but differing in that the same molar amount of Coupler Nos. (1), (11), (14) or (25) was used instead of Coupler No. (4) in Sample (A) and that the ratio of the coupler (g)/high boiling point organic solvent (mg) was changed to ½, other Samples (B), (C), (D) and (E) were obtained, respectively.

Further, Comparative Samples (F), (G) and (H) were formed, where the following Comparative Couplers (a), (b) and (c) were used, respectively.

Comparative Coupler (a)

-continued

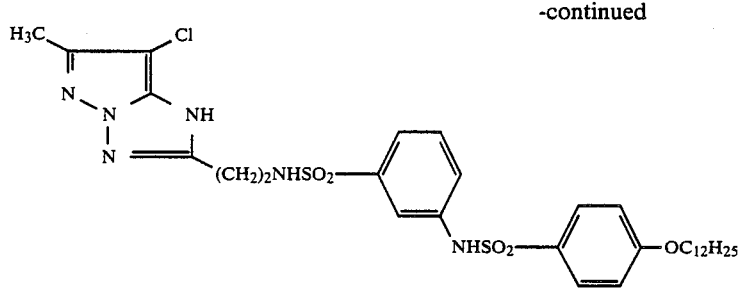

Comparative Coupler (b)

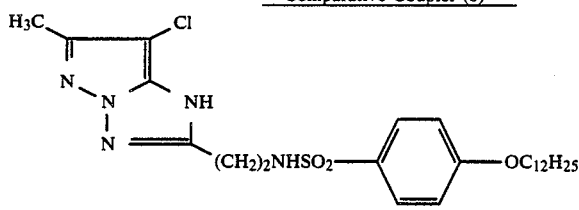

Comparative Coupler (c)

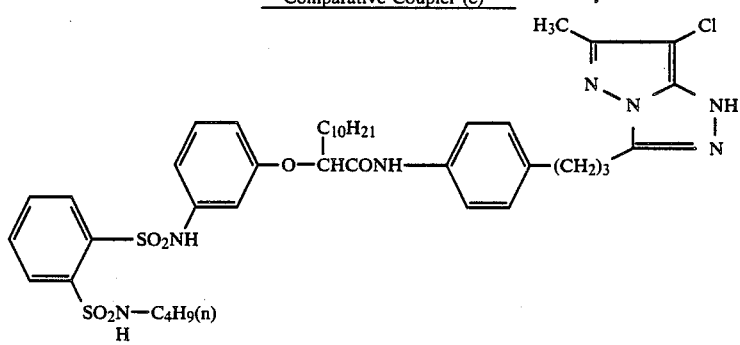

These samples were exposed to a red light through a continuous wedge and then developed in accordance with the following process:

| Processing Step | Temperature (°C.) | Time |
| --- | --- | --- |
| Development | 33 | 3 min 30 sec |
| Bleaching Fixation | 33 | 1 min 30 sec |
| Rinsing | 28–35 | 3 min |

The composition of each processing solution as used in the above steps was as follows:

Developer:

| | |
| --- | --- |
| Diethylenetriaminepentaacetic Acid | 1.0 g |
| Benzyl Alcohol | 15 ml |
| Diethylene Glycol | 10 ml |
| Na$_2$SO$_3$ | 2.0 g |
| KBr | 0.5 g |
| Hydroxylamine Sulfate | 3.0 g |
| 4-Amino-3-methyl-N—ethyl-N—[β-(methane-sulfonamido)ethyl]-p-phenylenediamine Sulfate | 5.0 g |
| Na$_2$CO$_3$ (monohydrate) | 30 g |
| Fluorescent Whitening Agent (4,4′-diaminostilbene type) | 1.0 g |

| -continued | |
| --- | --- |
| Water to make | 1 liter |
| pH | 10.1 |

Bleaching Fixation Solution:

| | |
| --- | --- |
| Ammonium Thiosulfate (70 wt % aq. soln.) | 150 ml |
| Na$_2$SO$_3$ | 15 g |
| NH$_4$[Fe(EDTA)] | 55 g |
| EDTA.2Na | 4 g |
| Water to make | 1 liter |
| pH | 6.9 |

The magenta color image thus formed in each sample was sharp and had a high chroma. The photographic characteristics of the color image of each sample was measured. Further, the samples were exposed to light with a Xenon Discoloration Tester (100,000 luxes) for 6 days to observe the degree of the discoloration of each sample. After the discoloration test, the density in the part which had had a density of 1.0 before the test was measured. For the measurement of the density, Macbeth Densitometer RD-514 was used. The results are given in the following Table 1.

TABLE 1

| Sample No. | Coupler | Photographic Characteristics | | | Light Discoloration Test (initial density: 1.0) (Xe discoloration tester, 6 days) | Note |
| --- | --- | --- | --- | --- | --- | --- |
| | | Sensitivity* | Gradation | Maximum Density | | |
| A | Coupler No. (4) | 100 | 2.82 | 2.55 | 0.84 | Present Invention |

TABLE 1-continued

| Sample No. | Coupler | Photographic Characteristics | | | Light Discoloration Test (initial density: 1.0) (Xe discoloration tester, 6 days) | Note |
|---|---|---|---|---|---|---|
| | | Sensitivity* | Gradation | Maximum Density | | |
| B | Coupler No. (1) | 98 | 2.79 | 2.53 | 0.80 | Present Invention |
| C | Coupler No. (11) | 101 | 2.83 | 2.57 | 0.83 | Present Invention |
| D | Coupler No. (14) | 102 | 2.82 | 2.62 | 0.80 | Present Invention |
| E | Coupler No. (25) | 97 | 2.71 | 2.38 | 0.68 | Present Invention |
| F | Comparative Coupler (a) | 85 | 2.45 | 2.26 | 0.68 | Comparative Sample |
| G | Comparative Coupler (b) | 81 | 2.36 | 2.21 | 0.63 | Comparative Sample |
| H | Comparative Coupler (c) | 79 | 2.10 | 1.95 | 0.48 | Comparative Sample |

Note:
*This represents the relative value of the reciprocal of the exposure to obtain a density of (fog + 0.5). (The sensitivity of Sample (A) was selected as 100.)

The results shown in Table 1 prove that the couplers having a sulfonamidophenylenesulfonamido group in accordance with the present invention have excellent photographic characteristics. In particular, the results of the light discoloration test prove that the couplers of the present invention having the substituent $R_5$ in the o-position of the benzenesulfonamido group, which is the nearest position to the skeleton of the coupler, have unexpectedly superior photographic characteristics, especially a higher color image fastness to light. Regarding the pyrazoloazole skeleton of the couplers, the above results show that the 1H-pyrazolo[1,5-b][1,2,4]triazole type couplers (i.e., Coupler Nos (4), (1), (11) and (14) are relatively superior to the 1H-pyrazolo[5,1-c][1,2,4]triazole type coupler, e.g., Coupler No. (25), with respect to photographic characteristics and color image fastness.

EXAMPLE 2

The following first layer (layer closest to the support) to seventh layer (outermost layer) were coated on a paper support having been laminated with polyethylene on both surfaces, as shown in the following Table 2, to obtain Color Photographic Material Samples (I), (J), (K) and (L).

The coating solution for the first layer was prepared as follows:

115 g of the yellow coupler (as shown in Table 2) was dissolved in a mixture solution comprising 100 ml of dibutyl phthalate (DBP) and 200 ml of ethyl acetate, and the resulting solution was emulsified and dispersed in 800 g of a 10% gelatin aqueous solution containing 80 ml of a 1% sodium dodecylbenzenesulfonate aqueous solution. Next, this emulsified dispersion thus prepared was blended with 1,450 g of a blue-sensitive silver chlorobromide emulsion (Br content: 80%, Ag content: 66.7 g) to obtain the coating solution for the first layer. The other coating solutions for the other layers were prepared in the same manner. Sodium 2,4-dichloro-6-hydroxy-s-triazine was used as a hardener in each layer.

The following spectral sensitizer was used in each layer:

Blue-Sensitive Emulsion Layer:
Sodium 3,3'-di($\gamma$-sulfopropyl)selenacyanine ($2 \times 10^{-4}$ mol per mol of silver halide)

Green-Sensitive Emulsion Layer:
Sodium 3,3'-di($\gamma$-sulfopropyl)-5,5'-diphenyl-9-ethyloxacarbocyanine ($2.5 \times 10^{-4}$ mol per mol of silver halide)

Red-Sensitive Emulsion Layer:
Sodium 3,3'-di($\gamma$-sulfopropyl)-9-methylthiadicarbocyanine ($2.5 \times 10^{-4}$ mol per mol of silver halide)

The following dye was used as an anti-irradiation dye in each emulsion layer:

Green-Sensitive Emulsion Layer:

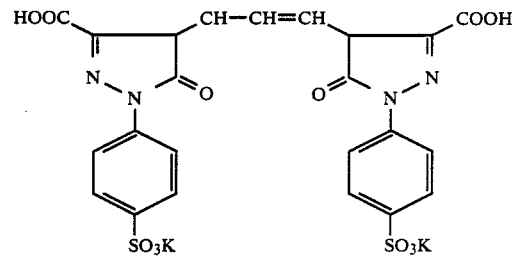

Red-Sensitive Emulsion Layer:

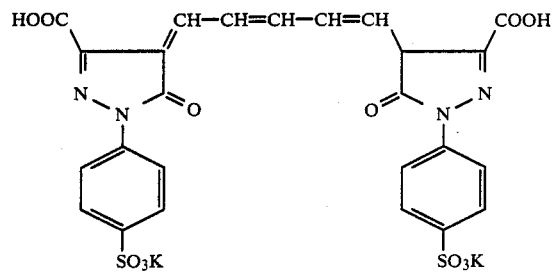

TABLE 2

| | |
|---|---|
| Seventh Layer: Protective Layer | |
| Gelatin | 1,500 mg/m² |
| Sixth Layer: UV Absorbent Layer | |
| UV absorbent (*f) | 180 mg/m² |
| UV absorbent solvent (TNP) | 80 mg/m² |
| Gelatin | 500 mg/m² |
| Fifth Layer: Red-Sensitive Layer | |
| Silver chlorobromide emulsion (silver bromide: 50 mol %) | Ag 250 mg/m² |
| Cyan coupler (*d/*e) | 180 mg/220 mg/m² |
| UV absorbent (*g) | 200 mg/m² |
| Cyan coupler solvent (TNP/DBP) | 200 mg/200 mg/m² |
| Gelatin | 1,000 mg/m² |
| Fourth Layer: UV Absorbent Layer | |
| UV absorbent (*f) | 60 mg/m² |
| UV absorbent solvent (TNP) | 200 mg/m² |
| Gelatin | 1,200 mg/m² |
| Third Layer: Green-Sensitive Layer | |
| Silver chlorobromide emulsion (silver bromide: 70 mol %) | Ag 200 mg/m² |
| Magenta coupler (see Table 3 for | |

TABLE 2-continued

| description and amount) | |
|---|---|
| Discoloration inhibitor | 200 mg/m² |
| Magenta coupler solvent (see | |
| Table 3 for description and amount) | |
| Gelatin | 1,300 mg/m² |
| Second Layer: Color Stain Inhibitory Layer | |
| Gelatin | 1,200 mg/m² |
| First Layer: Blue-Sensitive Layer | |
| Silver chlorobromide emulsion | 400 mg/m² |
| (silver bromide: 80 mol %) | |
| Yellow coupler (*a) | 690 mg/m² |
| Color stain inhibitor (*b) | 690 mg/m² |
| Yellow coupler solvent (DBP) | 1,000 mg/m² |
| Gelatin | 1,500 mg/m² |
| Support | |
| Paper support as laminated with polyethylene on both surfaces | |

In the above Table 2, TNP means trinonyl phosphate; DBP means dibutyl phthalate; TCP means tricresyl phosphate; TOP means tris(2-ethylhexyl)phosphate; and the compounds (*a) through (*g) have the following structural formulae:

(*a) Yellow Coupler:

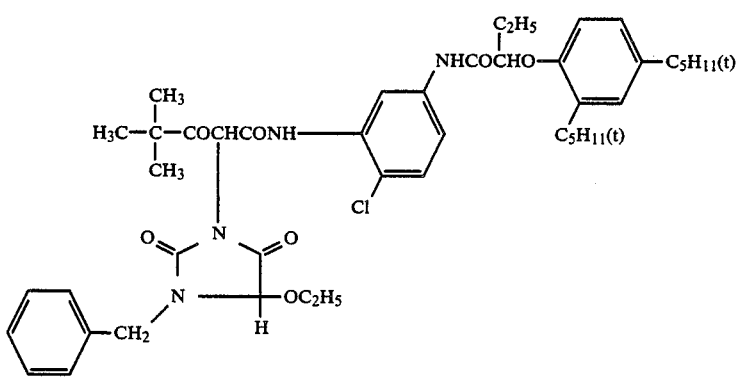

(*b) Discoloration Inhibitor:

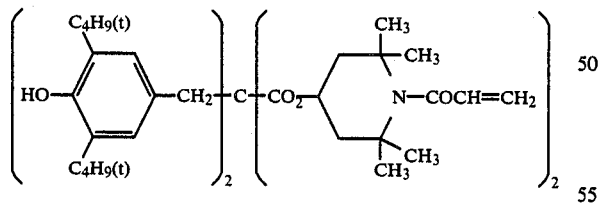

(*c) Discoloration Inhibitor:

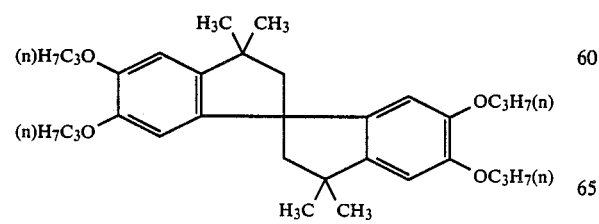

(*d) Cyan Coupler:

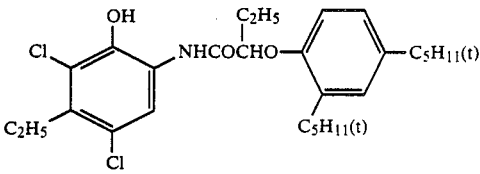

(*e) Cyan Coupler:

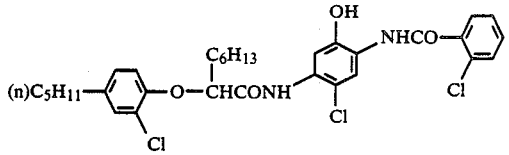

(*f) UV Absorbent:

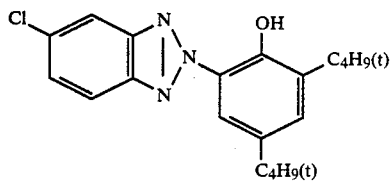

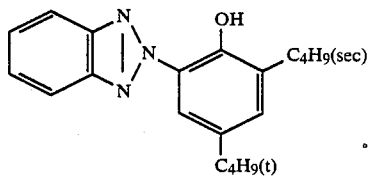

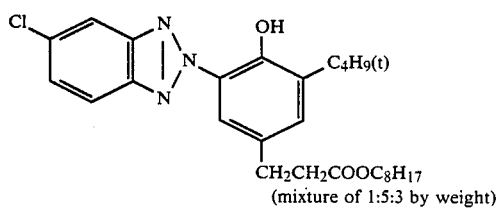

(mixture of 1:5:3 by weight)

(*g) UV Absorbent:

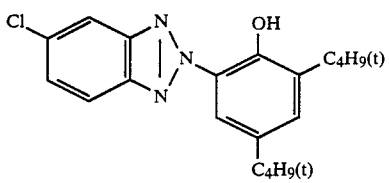

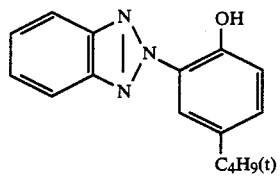

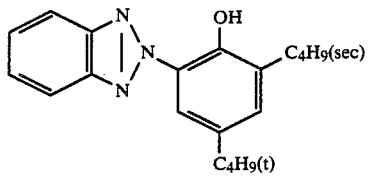

(mixture of 1:3:3 by weight)

TABLE 3

| Sample No. | Magenta Coupler (mg/m²) | Magenta Coupler Solvent (mg/m²) | Note |
|---|---|---|---|
| I | Coupler (1) (370) | TCP/TOP (370/370) | Present Invention |
| J | Coupler (4) (380) | TCP/TOP (380/380) | Present Invention |
| K | Coupler (11) (450) | TCP/TOP (450/459) | Present Invention |
| L | Comparative Coupler (a) (320) | TCP/TOP (320/320) | Comparative Sample |

These samples were exposed to a green light through a continuous wedge and then developed in the same manner as in Example 1.

The photographic characteristics of each of the thus processed samples were measured. Next, the samples were exposed to light with a fluorescent light discoloration tester (15,000 luxes) for 8 weeks, and the magneta color density of each sample in the part which had had an initial density of 1.0 was measured. The results are given in the following Table 4.

TABLE 4

| Sample No. | Coupler | Photographic Characteristics Gradation | Maximum Density | Light Discoloration Test (initial density: 1.0) (fluorescent light discoloration tester, 8 weeks) | Note |
|---|---|---|---|---|---|
| I | Coupler (1) | 2.57 | 2.20 | 0.83 | Present Invention |
| J | Coupler (4) | 2.62 | 2.25 | 0.88 | Present Invention |
| K | Coupler (11) | 2.63 | 2.26 | 0.87 | Present Invention |
| L | Comparative Coupler (a) | 2.25 | 1.98 | 0.69 | Comparative Sample |

The surprisingly superior effects which are obtained when color photographic materials employing magenta couplers in accordance with the present invention are apparent from the above experiments. In particular, the results shown in Table 1 and Table 4 prove that photographic materials incorporating couplers of the present invention are superior in the photographic characteristics and colorability as well as in light fastness of the color images formed therefrom.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having at least one silver halide emulsion layer coated thereon, wherein a pyrazoloazole type coupler of general formula (I) is present in said at least one silver halide emulsion layer or an adjacent layer thereto:

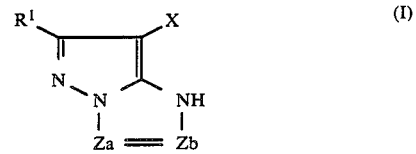

wherein Za and Zb each may represent

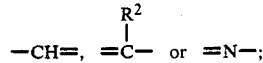

$R^1$ and $R^2$ each may represent a hydrogen atom or a substituent; X represents a hydrogen atom; a group bonded via a nitrogen atom or a group bonded via a sulfur atom, each of which is removed upon a coupling reaction with an oxidized form of an aromatic primary amine type developing agent; when Za=Zb is a carbon-carbon double bond, this may be a part of the aromatic ring in the formula; with the proviso that at least one of $R^1$ and $R^2$ is a group represented by general formulae (II) or (III):

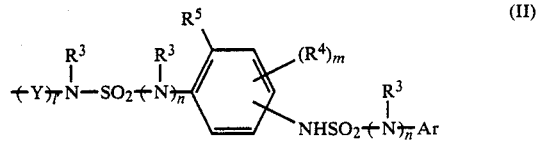

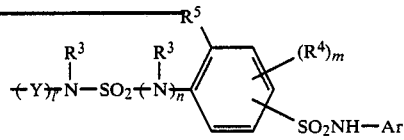

wherein $R^3$ represents a hydrogen atom or a substituted or unsubstituted alkyl group; $R^4$ represents a hydrogen atom or a substituent; $R^5$ represents a halogen atom, a substituted or unsubstituted alkoxy, aryloxy, amino, alkylthio or arylthio group; Ar represents an aryl group; Y represents an alkylene group or an arylene group; l' is an integer of 0 or 1; n is an integer of 0 or 1; and m is an integer of 1 to 3; and that when $R^1$ represents an alkyl group or Y represents an alkylene group, the alkyl or alkylene group is a group of which the carbon atom directly bonded to the pyrazoloazole nucleus is a primary carbon.

2. The silver halide color photographic material as claimed in claim 1, wherein the pyrazoloazole type coupler is represented by general formulae (IV), (V), (VI), (VII) or (VIII):

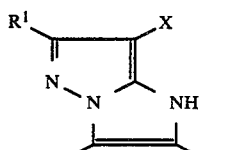
(IV)

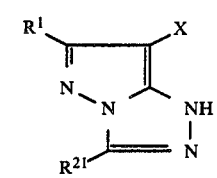
(V)

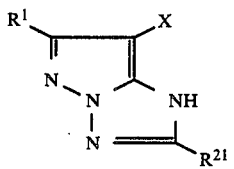
(VI)

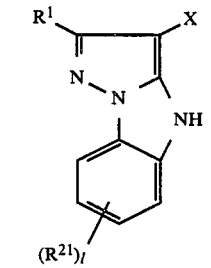
(VII)

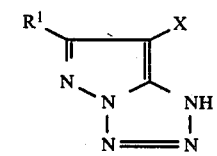
(VIII)

wherein $R^1$ and X have the same meanings as defined in claim 1; $R^{21}$ and $R^{22}$ have the same meanings as $R^2$ as defined in claim 1; and l is an integer of 1 to 4.

3. The silver halide color photographic material as claimed in claim 2, wherein $R^1$, $R^{21}$ and $R^{22}$ each may represent a hydrogen atom, a halogen atom, a substituted or unsubstituted alkyl group, an aryl group, a heterocyclic group, a cyano group, a hydroxyl group, a substituted or unsubstituted alkoxy group, an aryloxy group, a heterocyclic oxy group, an acyloxy group, a carbamoyloxy group, a silyloxy group, a sulfonyloxy group, an acylamino group, an anilino group, an amino group, a ureido group, an imido group, a sulfamoylamino group, a substituted or unsubstituted alkylthio group, an arylthio group, a heterocyclic thio group, a substituted or unsubstituted alkoxycarbonylamino group, an aryloxycarbonylamino group, a sulfonamido group, a carboxyl group, a carbamoyl group, an acyl group, a sulfamoyl group, a sulfonyl group, a sulfinyl group, a substituted or unsubstituted alkoxycarbonyl group or an aryloxycarbonyl group.

4. The silver halide color photographic material as claimed in claim 1, wherein X represents said group bonded via a sulfur atom.

5. The silver halide color photographic material as claimed in claim 1, wherein $R^3$ in general formulae (II) or (III) is a hydrogen atom.

6. The silver halide color photographic material as claimed in claim 2, wherein the pyrazoloazole type coupler is represented by general formulae (IV), (V) or (VI):

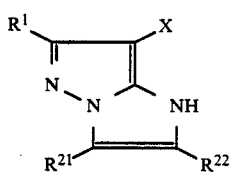
(IV)

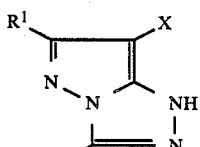
(V)

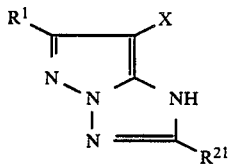
(VI)

wherein $R^1$ and X have the same meanings as defined in claim 1, and $R^{21}$ and $R^{22}$ have the same meanings as $R^2$ as defined in claim 1.

7. The silver halide color photographic material as claimed in claim 6, wherein the pyrazoloazole type coupler is represented by general formula (VI):

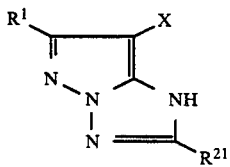
(VI)

wherein $R^1$ and X have the same meanings as defined in claim 1, and $R^{21}$ has the same meaning as $R^2$ as defined in claim 1.

8. The silver halide color photographic material as claimed in claim 1, wherein X represents said hydrogen atom.

9. The silver halide color photographic material as claimed in claim 1, wherein X represents said group bonded via a nitrogen atom.

* * * * *